United States Patent [19]

Boden et al.

[11] Patent Number: 5,077,275
[45] Date of Patent: Dec. 31, 1991

[54] ACYLATED BICYCLOALKADIENE-COMPOUND-CONTAINING COMPOSITIONS OF MATTER PROCESS FOR PREPARING SAME AND PERFUMERY USES THEREOF

[75] Inventors: Richard M. Boden, Ocean; Joseph A. McGhie, South Orange, both of N.J.

[73] Assignee: International Flavors & Fragrances Inc., New York, N.Y.

[21] Appl. No.: 701,849

[22] Filed: May 17, 1991

[51] Int. Cl.$^5$ ............................................... A61K 7/46
[52] U.S. Cl. ......................................... 512/17; 512/8; 568/374; 568/375; 568/356
[58] Field of Search ...................... 512/8, 17; 568/374, 568/375, 356

[56] References Cited

U.S. PATENT DOCUMENTS

| | | | |
|---|---|---|---|
| 3,754,036 | 8/1973 | Blumenthal | 512/8 |
| 3,929,675 | 12/1975 | Lemberg | 512/8 |
| 3,935,253 | 1/1976 | Naegeli | 568/374 |
| 3,966,819 | 6/1976 | Schulte-Elte et al. | 512/17 |
| 4,393,245 | 7/1983 | Hoffman et al. | 512/8 |
| 4,853,368 | 8/1989 | Neinhaus et al. | 512/8 |

Primary Examiner—James H. Reamer
Attorney, Agent, or Firm—Arthur L. Liberman

[57] ABSTRACT

Described are acylated bicycloalkadiene-compound-containing compositions of matter, mixtures of compounds containing predominantly compounds having the structures:

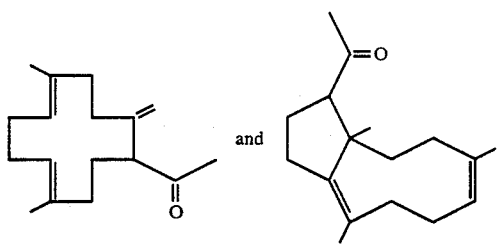

with the compositions of matter containing from 50 up to 100% of the compound having the structure:

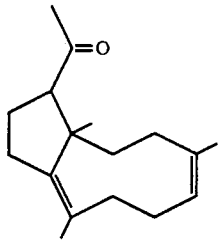

prepared by reacting the compound having the structure:

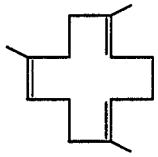

or a mixture containing, predominently, the compound having the structure:

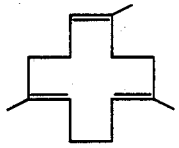

with acetic anhydride in the presence of a Lewis acid catalyst such as boron trifluoride etherate.

Also described are perfumery uses of such compositions of matter for augmenting or enhancing the aroma of perfume compositions, colognes or perfumed articles such as solid or liquid anionic, cationic, nonionic or zwitterionic detergents, cosmetic powders, hair preparations and the like.

12 Claims, 11 Drawing Sheets

GLC PROFILE FOR EXAMPLE I.
(CAPILLARY SURVEY).

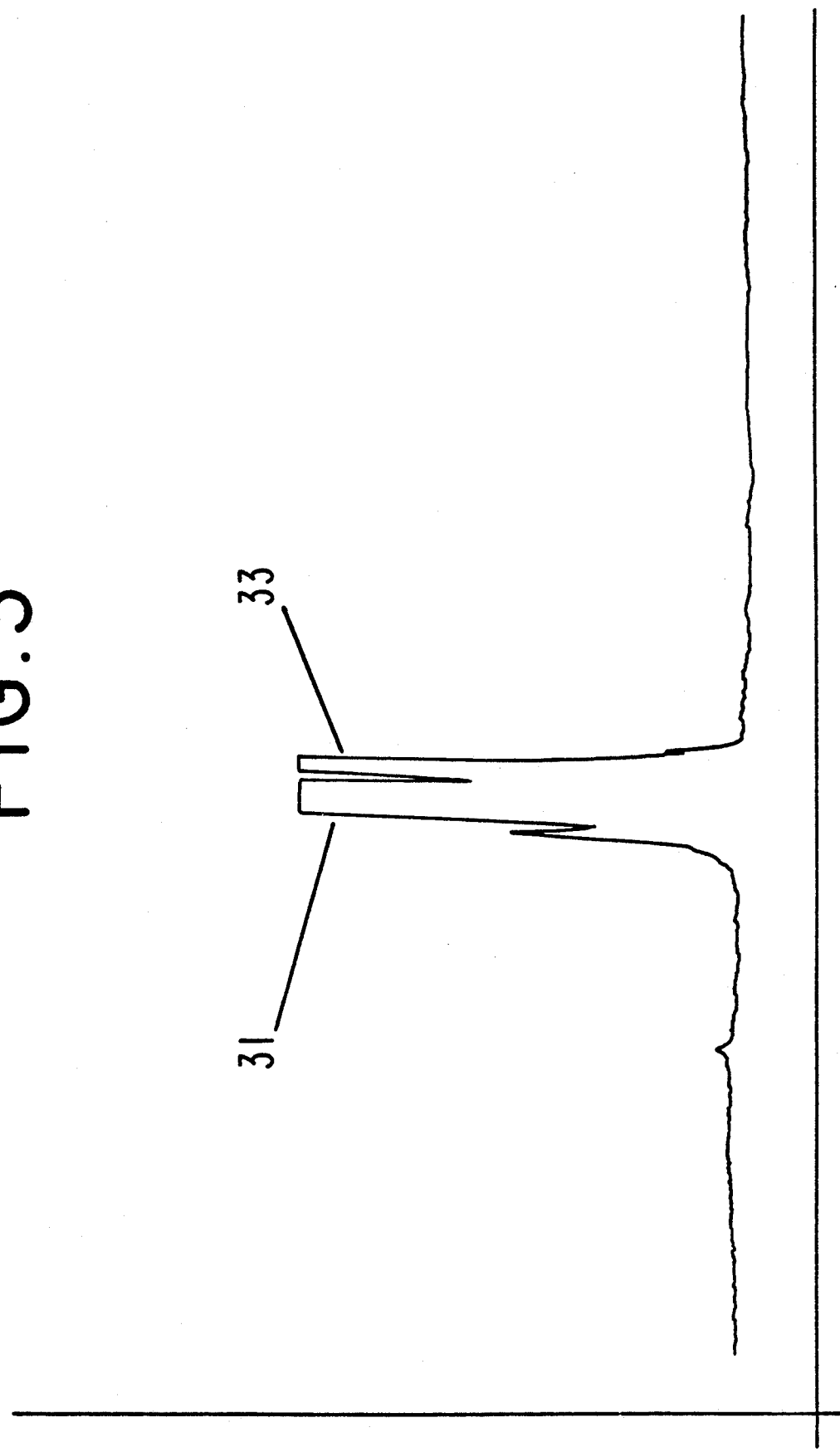

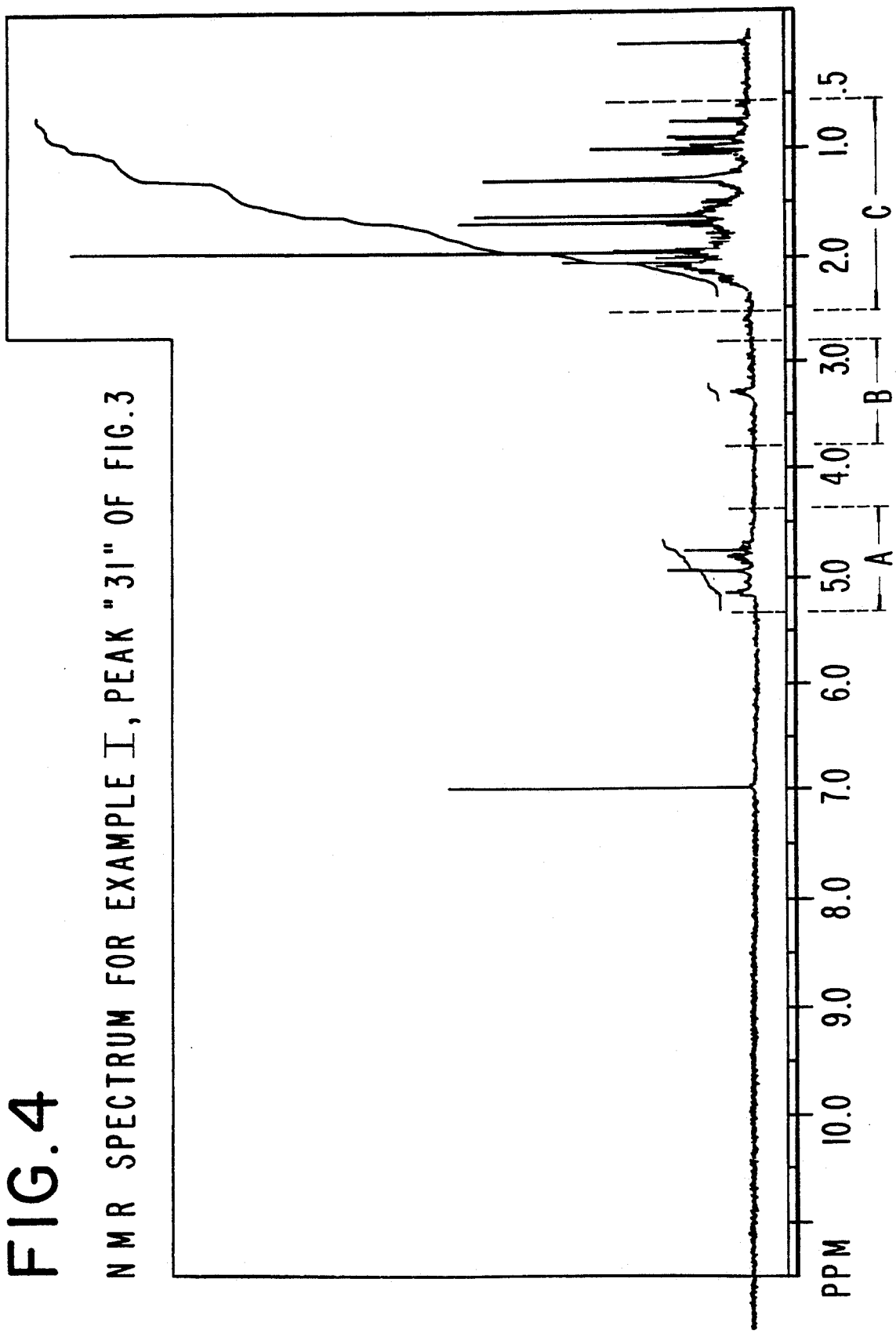
FIG. 4 NMR SPECTRUM FOR EXAMPLE I, PEAK "31" OF FIG. 3

FIG.4-A
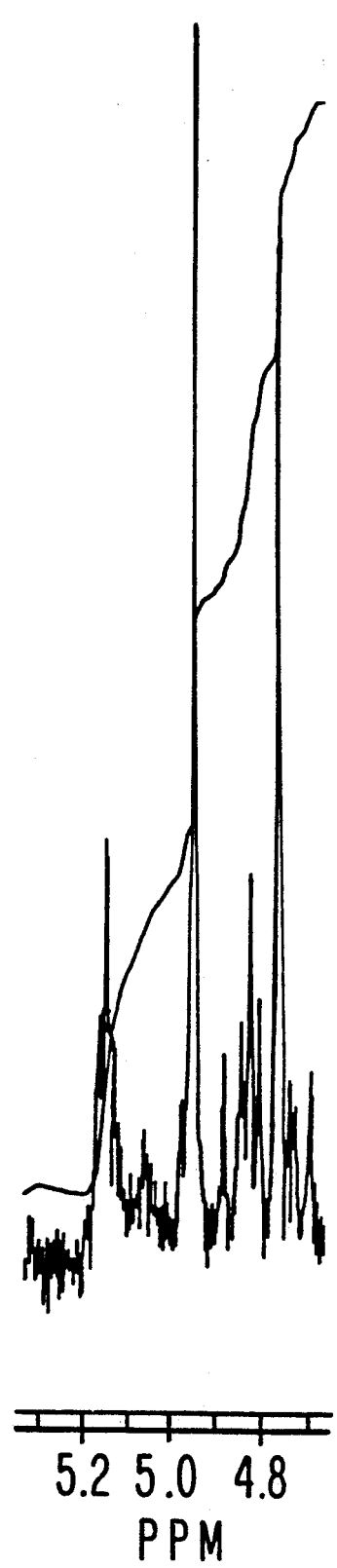
5.2 5.0 4.8
PPM
FIG.4-B
PPM

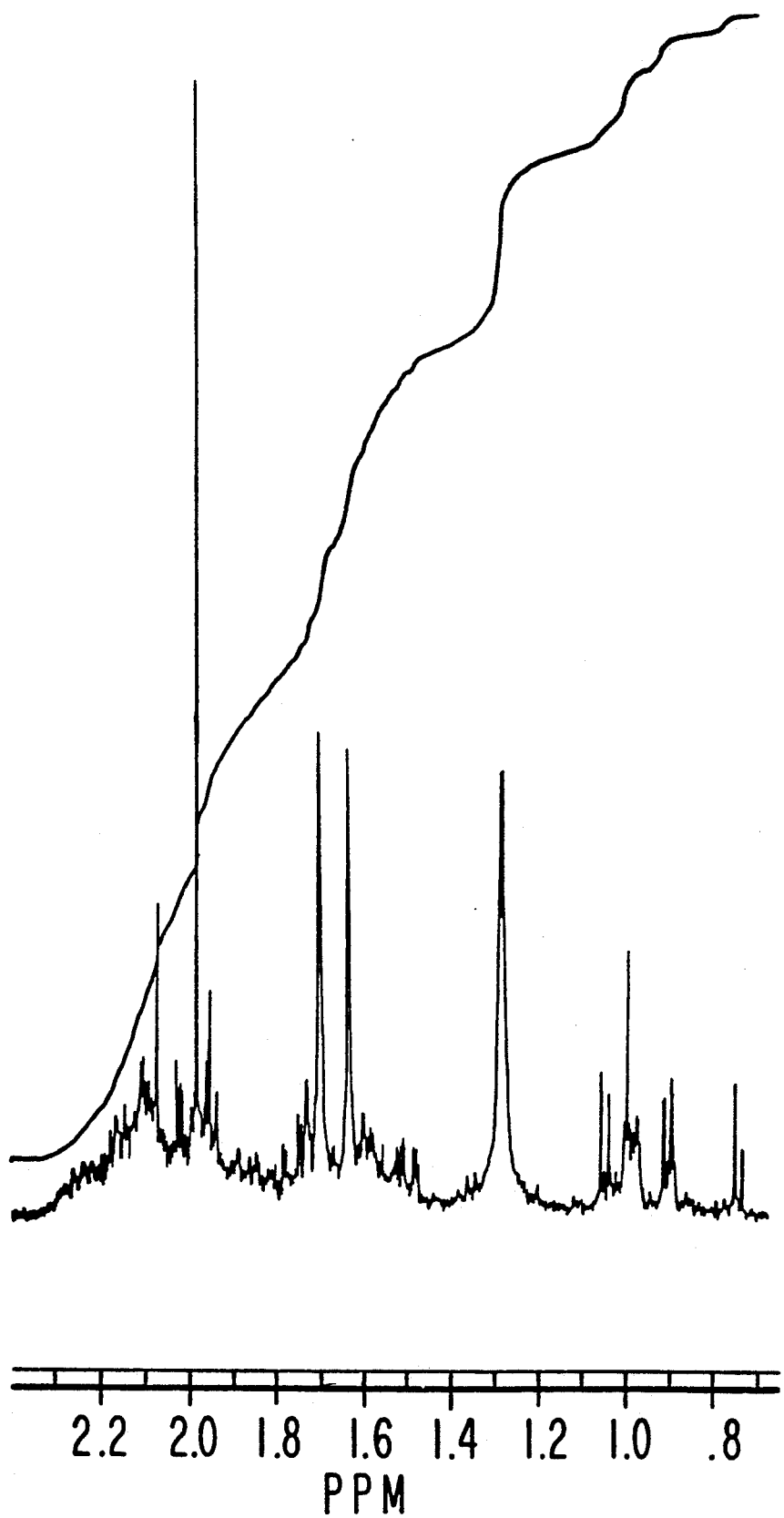
FIG. 4-C

IR SPECTRUM FOR EXAMPLE I, PEAK "31" OF FIG. 3.

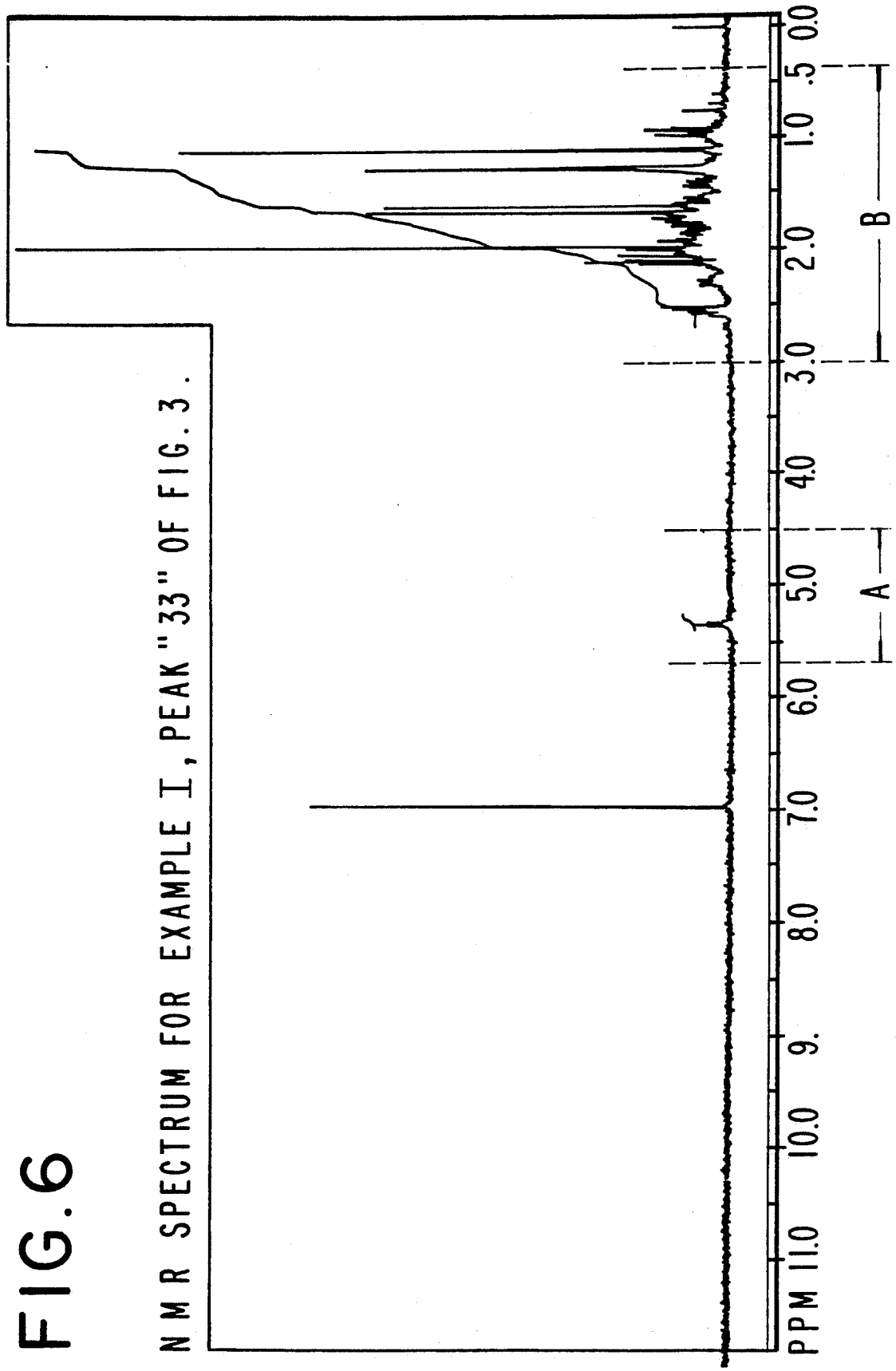
FIG. 6 NMR SPECTRUM FOR EXAMPLE I, PEAK "33" OF FIG. 3.

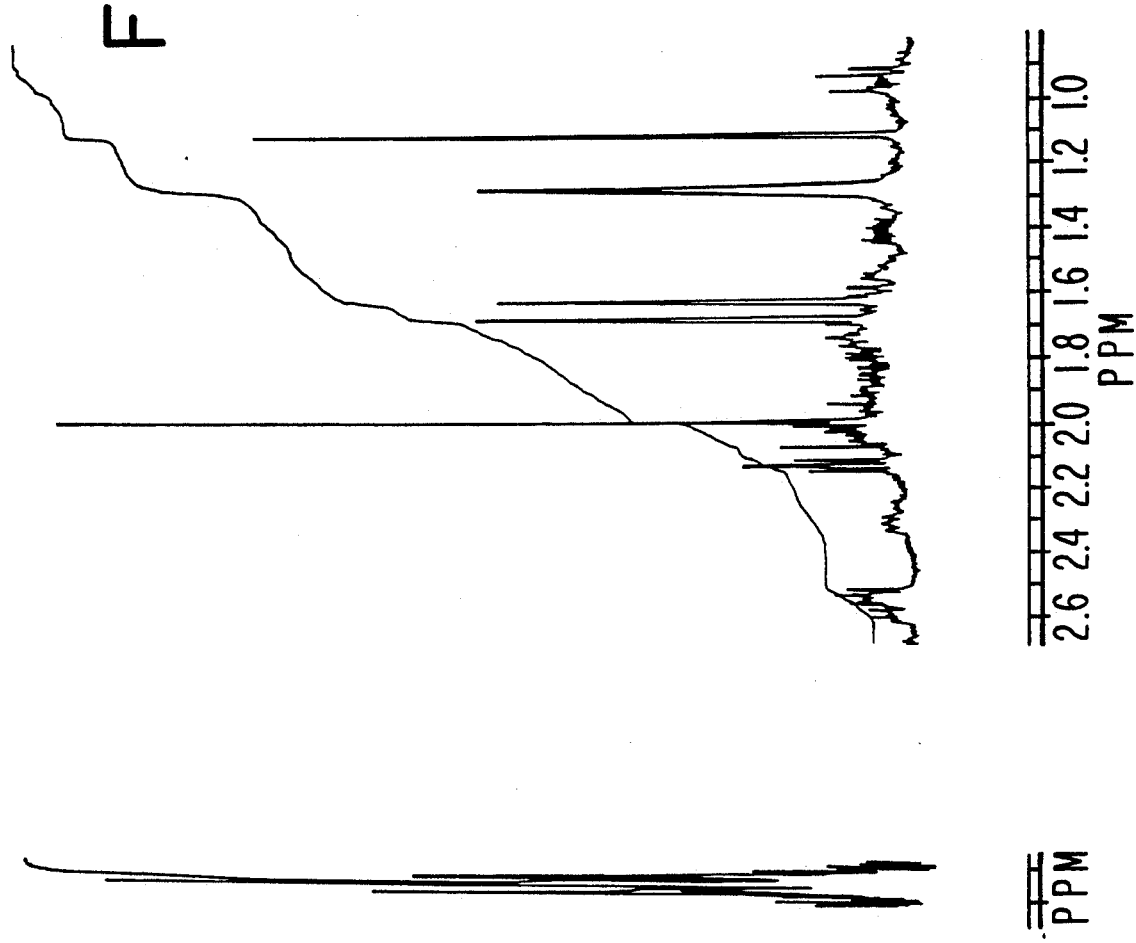

IR SPECTRUM FOR EXAMPLE I, PEAK "33" OF FIG. 3.

ACYLATED BICYCLOALKADIENE-COMPOUND-CONTAINING COMPOSITIONS OF MATTER PROCESS FOR PREPARING SAME AND PERFUMERY USES THEREOF

BACKGROUND OF THE INVENTION

Whereas the present invention relates to acylated bicycloalkadiene-compound-containing compositions of matter containing from 50 to 100% of the compound having the structure:

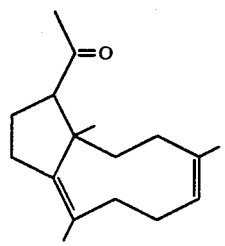

and from 0 up to 50% of the compound having the structure:

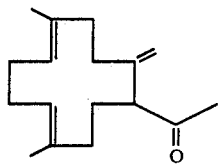

and perfumery uses thereof.

There has been considerable work performed relating to substances which can be used to impart (modify, augment or enhance) fragrances to (or in) various consumable materials. These substances are used to diminish the use of natural materials some of which may be in short supply and to provide more uniform properties in the finished product.

Long-lasting and substantive vetiver, peppery, woody, patchouli, musky, camphoraceous and amber aromas with sweet, musky, vetiver, peppery and ambery topnotes are highly desirable in in several types of perfume compositions, perfumed articles and colognes (e.g., sandalwood, vetiver and patchouli fragrances and after shave lotions).

The perfume uses of acylated unsaturated alicyclic compounds is well known in the prior art.

Hall, U.S. Pat. No. 3,816,349 issued on June 11, 1974 discloses such compounds and indicates their ambery, woody and camphoraceous quality. The Hall reference discloses compounds defined according to the structure:

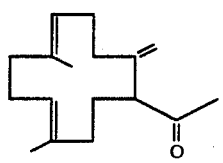

prepared from compounds defined according to the structure:

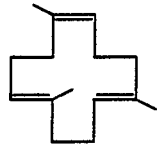

according to the reaction:

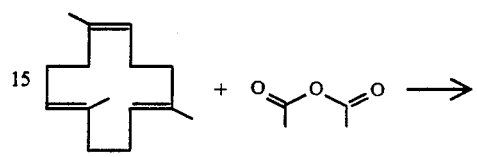

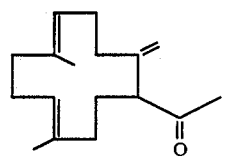

which takes place in the presence of a Lewis acid catalyst.

However, the compositions of matter produced according to the Hall reference do not have nearly the same quality, intensity or substantivity and do not have even similar aroma characteristics that the acylated bicycloalkadiene-compound-containing compositions of matter of our invention possess.

Shell Fine Chemicals, Technical Bulletin FC:82:153:TB discloses the compounds having the structure:

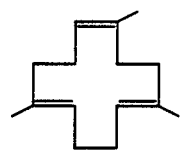

and its properties and indicates that this compound as well as the compound having the structure:

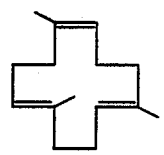

can be used in the preparation of perfume ingredients and that among the literature references mentioned are U.S. Letter Pat. No. 3,929,675 as well as South African Patent 68/05548. It is further indicated in the Shell Technical Bulletin that "mono cyclic alkyl ketones useful as perfumery ingredients can be made in a process involving the acylation of olefins such as 1,5,9-trimethyl-1,5,9-cyclododecatriene". This material has the structure:

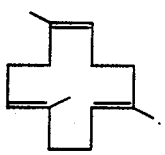

There is however no inference in the Shell Technical Bulletin that the compound having the structure:

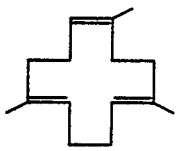

can be used to create a composition of matter containing from 50 to 100% of the compound having the structure:

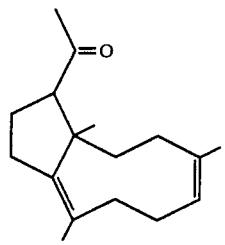

or that such composition of matter has the unexpected, unobvious and advantageous perfumery properties that the compositions of matter of our invention possess.

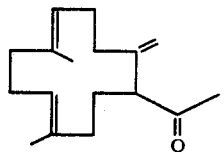

(Conditions: 50 meter ×0.32 mm carbowax 20M column programmed from 75°-225° C. at 2° C. per minute).

Figure 2:
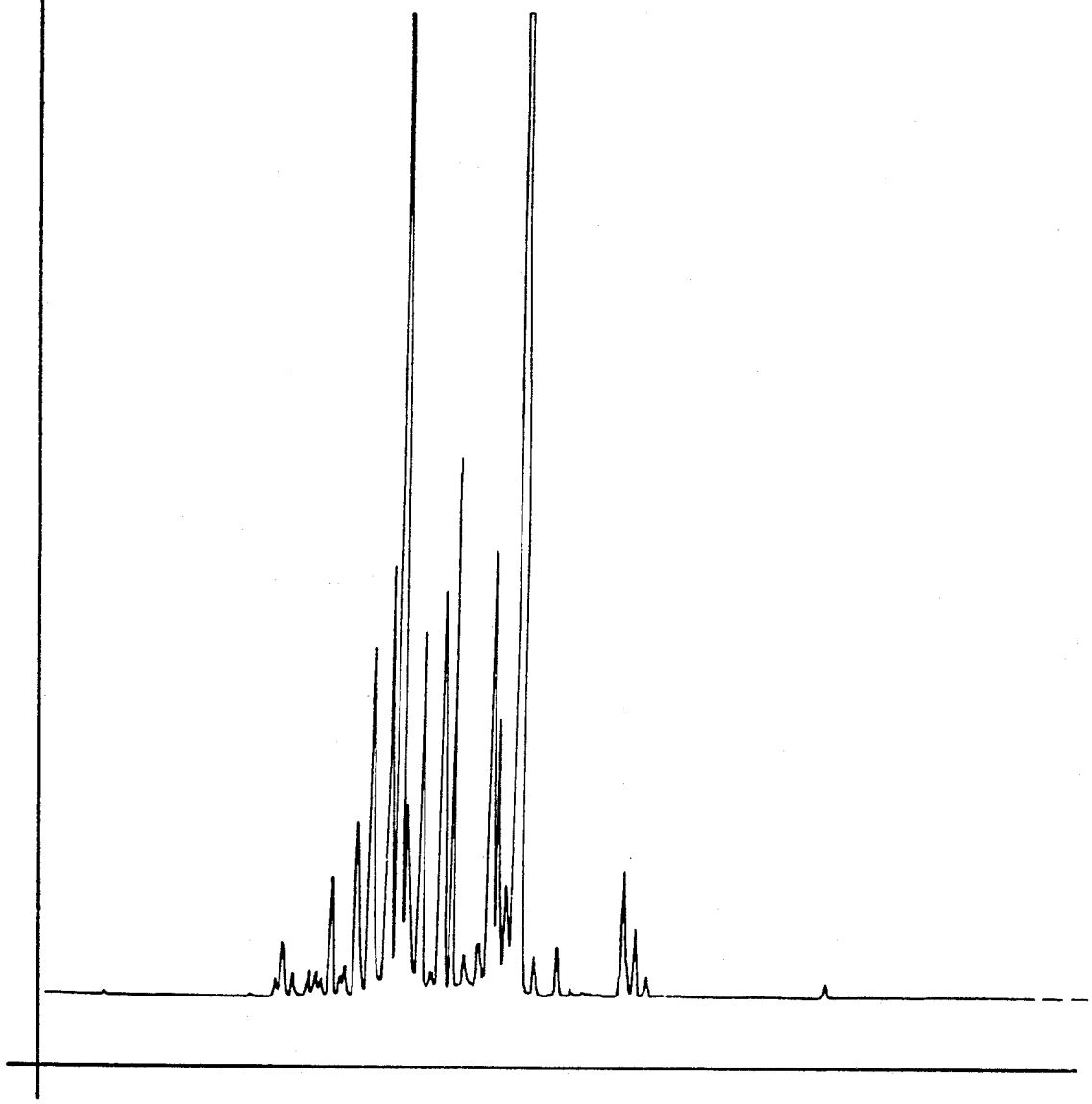

FIG. 2 is the GLC profile (capillary survey) for the reaction product of Example I containing the compounds having the structures:

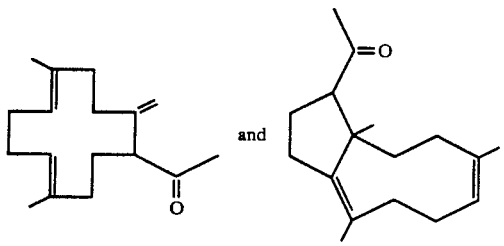

(Conditions: 50 meter ×0.32 mm fused silica carbowax 20M column programmed at 75°-225° C. per minute).

FIG. 3 is the GLC profile for the reaction product of Example I containing the compounds having the structures:

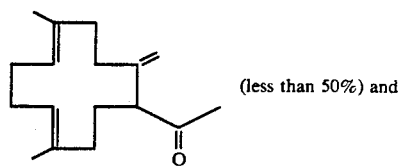

(less than 50%) and

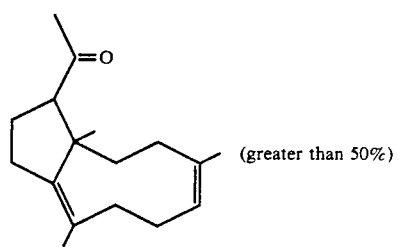

(greater than 50%)

(Conditions: SE-30 column programmed at 100°-220° C. at 8° C. per minute).

FIG. 4 is the NMR spectrum for the peak indicated by reference numeral 31 of FIG. 3 for the compound having the structure:

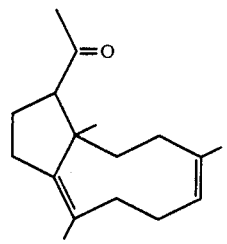

FIGS. 4A, 4B and 4C are detailed sections "A", "B" and "C" of the NMR spectrum of FIG. 4, respectively.

Figure 5:
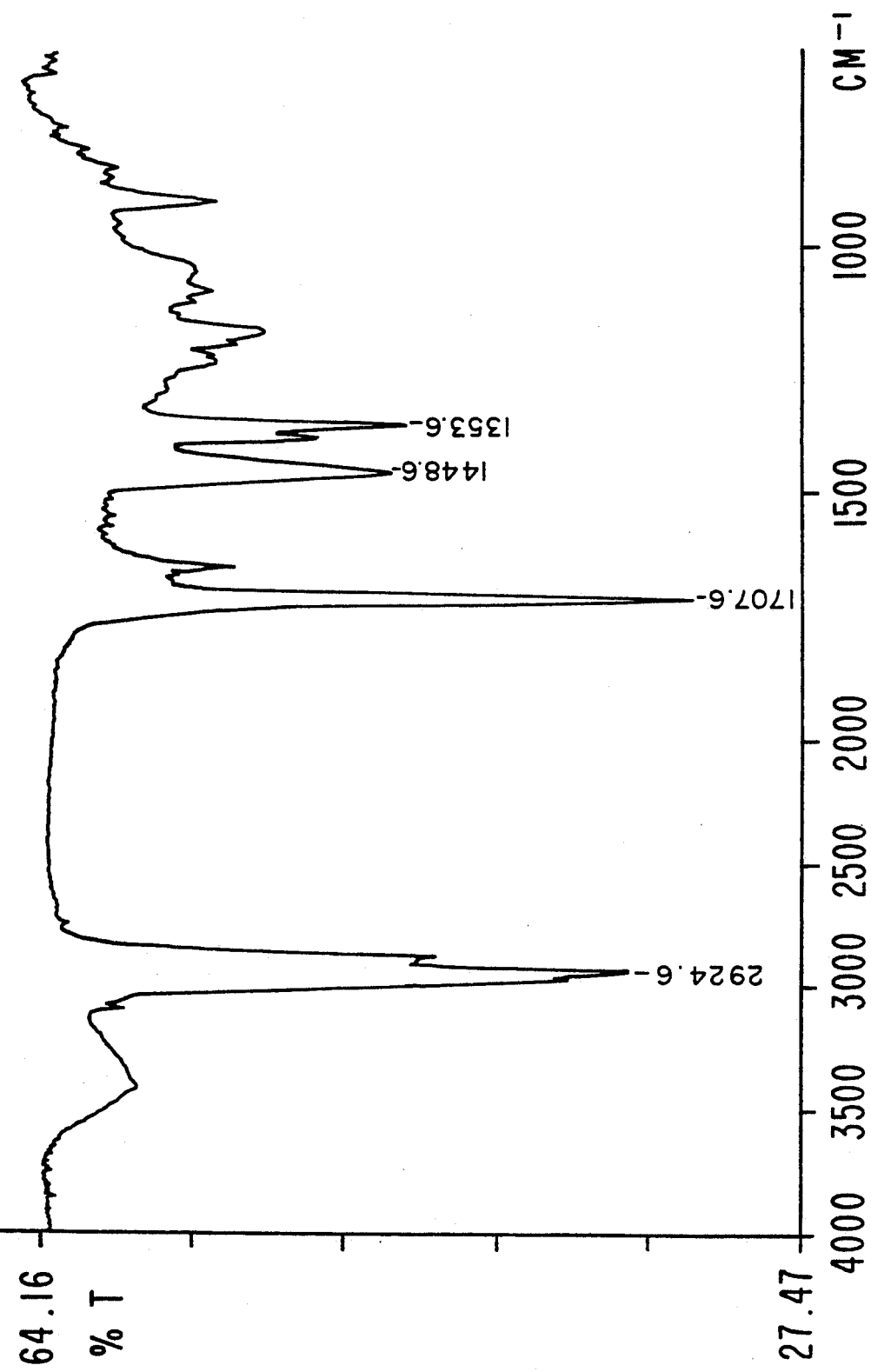

FIG. 5 is the infra-red spectrum for the compound having the structure:

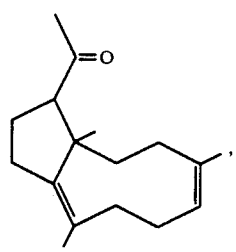

peak 31 of FIG. 3.

FIG. 6 is the NMR spectrum for peak 33 of FIG. 3, for the compound having the structure:

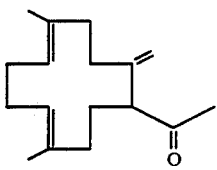

prepared according to Example I.

FIGS. 6A and 6B are detailed sections "A" and "B" of the NMR spectrum of FIG. 6.

Figure 7:
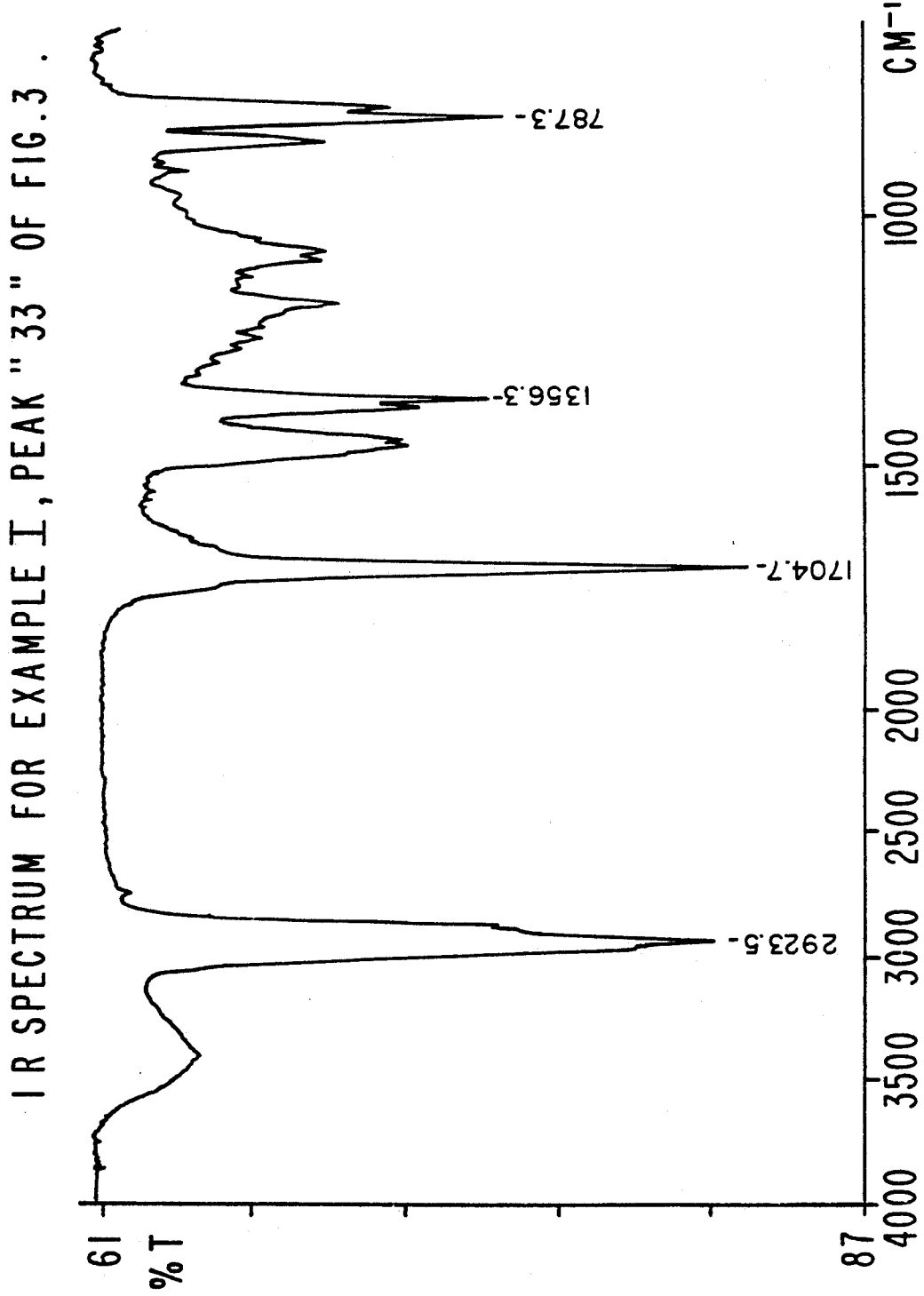

FIG. 7 is the infra-red spectrum for peak 33 of FIG. 3, for the compound having the structure:

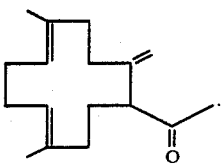

Figure 8:
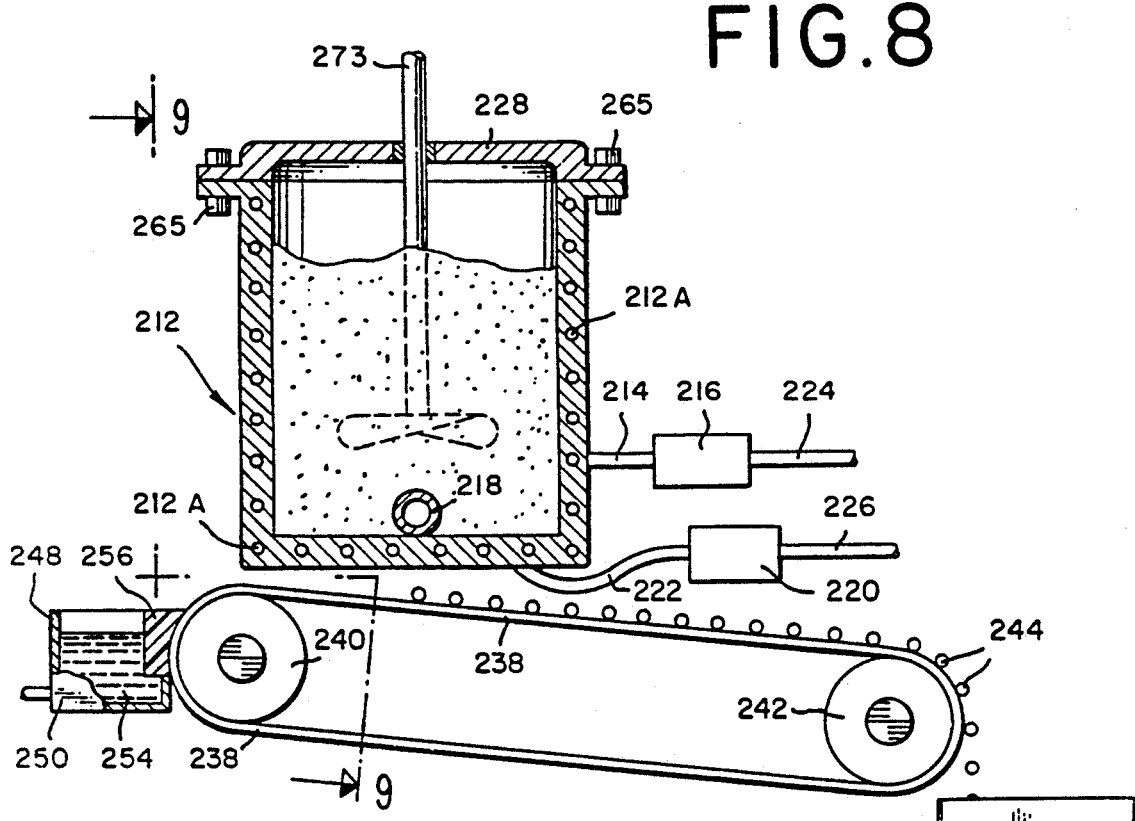

FIG. 8 represents a cut-away side elevation view of apparatus used in forming perfumed polymers which contain imbedded therein at least one of the acylated bicyclo-alkadiene-compound-containing compositions of matter of our invention.

Figure 9:
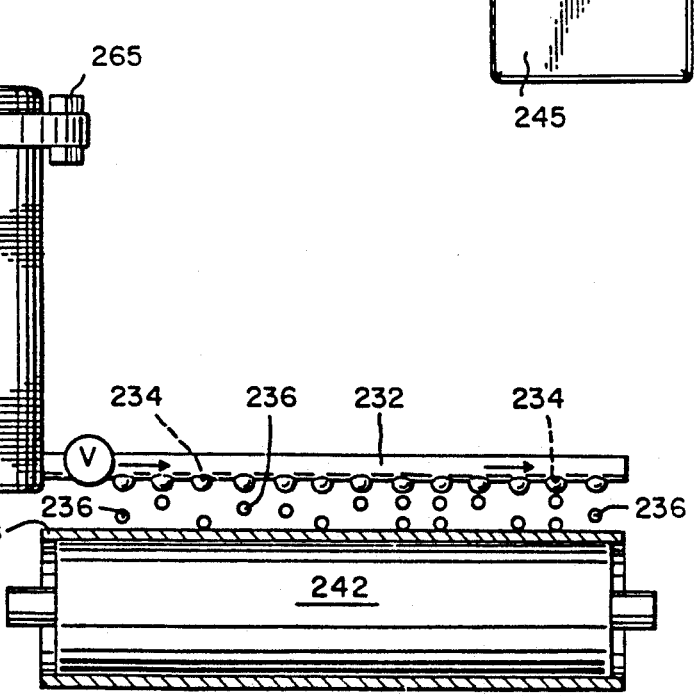

FIG. 9 is a front view of the apparatus of FIG. 8 looking in the direction of the arrows. cl DETAILED DESCRIPTION OF THE DRAWINGS FIG. 3 is the GLC profile for the reaction product of Example I (conditions: SE-30 column programmed at 100°-220° C. at 8° C. per minute). The peak indicated by reference 31 is the peak for the compound having the structure:

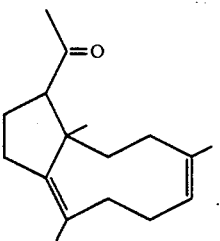

The peak indicated by reference 33 is the peak for the compound having the structure:

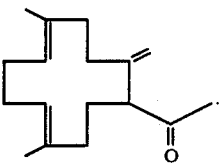

FIG. 4 is the NMR spectrum for the peak indicated by reference 31 of FIG. 3. Sections "A", "B" and "C" are shown in detail in FIGS. 4A, 4B and 4C, respectively.

FIG. 6 is the NMR spectrum for the peak indicated by reference numeral 33 of FIG. 3. Sections "A" and "B" are shown in detail in FIGS. 6A and 6B, respectively.

Referring to FIGS. 8 and 9, there is provided a process for forming scented polymer elements (wherein the polymer may be a thermoplastic polymer such as low density polyethylene or polypropylene or copolymers of ethylene and vinyl acetate or mixtures of polymers and copolymers such as copolymers of ethylene and vinyl acetate and polyethylene) such pellets useful in the formation of plastic particles useful in fabricating certain articles which may be perfumed This process comprises heating the polymer or mixture of polymers to the melting point of said polymer or mixture of polymers, e.g., 250° C. in the case of low density polyethylene. The lower most portion of the container is maintained at a slightly lower temperature and the material in the container is taken off at such location for delivery through the conduit. Thus, referring to FIGS. 8 and 9, in particular, the apparatus used in producing such elements comprises a device for forming the polymer containing the perfume, e.g., polyethylene or polyethylene-polyvinyl acetate or mixtures of same or polypropylene, which comprises a vat or container 212 into which the polymer taken alone or in admixture with other copolymers and the perfuming substance which is at least one of the acylated bicycloalkadiene-compound-containing compositions of matter of our invention and other compatible perfumes is placed. The container is closed by means of an air-tight lid 228 and clamped to the container by bolts 265. A stirrer 273 traverses the lid or cover 228 in an air-tight manner and is rotatable in a suitable manner. A surrounding cylinder 212A having heating coils which are supplied with electric current through cable 214 from a rheostat or control 216 is operated to maintain the temperature inside the container 212 such that the polymer in the container will be maintained in the molten or liquid state. It has been found advantageous to employ polymers at such a temperature that the viscosity will be in the range of 90-100 sayboldt seconds. The heater 218 is operated to maintain the upper portion of the container 212 within a temperature range of, for example, 220°-270° C. in the case of low density polyethylene. The bottom portion of the container 212 is heated by means of heating coils 212A regulated through the control 220 connected thereto through a connecting wire 222 to maintain the lower portion of the container 212 within a temperature range of 220°-270° C.

Thus, the polymer or mixture of polymers added to the container 212 is heated from 10-12 hours, whereafter the perfume composition or perfume material which contains one or more of the acylated bicycloalkadiene-compound-containing compositions of matter of our invention is quickly added to the melt Generally, about 10-45 percent by weight of the resulting mixture of the perfumery substance is added to the polymer.

After the perfume material is added to the container 212, the mixture is stirred for a few minutes, for example, 5-15 minutes and maintained within the temperature ranges indicated previously by the heating coil 212A. The controls 216 and 220 are connected through cables 224 and 226 to a suitable supply of electric current for supplying the power for heating purposes.

Thereafter, the valve "V" is opened permitting the mass to flow outwardly through conduit 232 having a multiplicity of orifices 234 adjacent to the lower side thereof. The outer end of the conduit 232 is closed so that the liquid polymer in intimate admixture with one or more of the acylated bicyclo-alkadiene-compound-containing compositions of matter of our invention and one or more other substances, will continuously drop or drip through the orifices 234 downwardly from the conduit 232. During this time, the temperature of the polymer intimately admixed with the perfumery substance in the container 212 is accurately controlled so that a temperature in the range of from about 240°-250° C., for example, (in the case of low density polyethylene) will exist in the conduit 232. The regulation of the temperature through the controls 216 and 220 is essential in order to insure the temperature balance to provide for the continuous dripping or dropping of molten polymer intimately admixed with the perfume substance which is all of or which contains one of the acylated bicycloalkadiene-compound-containing compositions of matter of our invention, through the orifices 234 at a rate which will insure the formation of droplets 236 which will fall downwardly onto a moving conveyor belt 238 caused to run between conveyor wheels 240 and 242 beneath the conduit 232.

When the droplets 236 fall onto the conveyor 238, they form pellets 244 which harden almost instantaneously and fall off the end of the conveyor 238 into a container 250 which is advantageously filled with water or some other suitable cooling liquid to insure the rapid cooling of each of the pellets 244. The pellets 244 are then collected from the container 250 and utilized for the formation of functional products, e.g., garbage bags and the like.

THE INVENTION

The present invention provides acylated bicycloalkadiene-compound-containing compositions of matter containing from 50-100 percent of the compound having the structure:

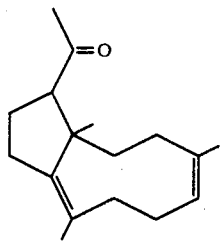

and containing from 0 to 50 percent of the compound having the structure:

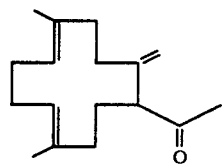

prepared according to the process of reacting the compound having the structure:

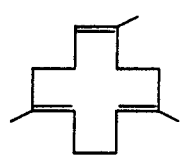

with acetic anhydride in the presence of a Lewis acid catalyst according to the reaction:

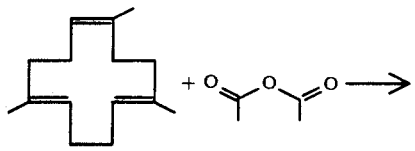

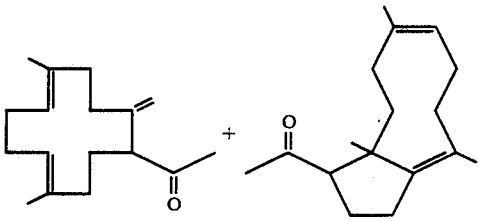

The acylated bicycloalkadiene-compound-containing compositions of matter of our invention produced according to the processes of our invention are capable of augmenting or enhancing vetiver, peppery, woody, patcholi, musky and camphoraceous aromas, with sweet, musky, vetiver, peppery and ambery topnotes. On a scale of "1-10", the quality of the formulations of our invention is rated at "9"; the intensity is rated at "9" and the substantivity is rated at "9". As comparison, compounds prepared by reacting the compound having the structure:

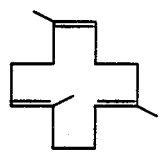

with acetic anhydride according to the reaction:

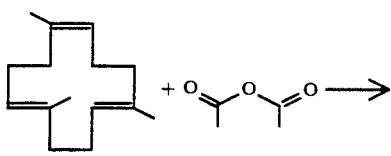

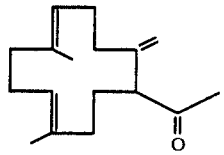

to prepare compositions of matter containing primarily the compound having the structure:

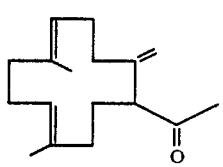

have woody, ambery and camphoraceous aromas with the quality intensity and substantivity being rated on a scale of "1-10", thusly:

quality: 8
intensity: 4
substantivity: 3.

The acylation can be carried out in the presence of a solvent or other vehicle. The vehicle, if used, can be a liquid which is inert to the reactants, catalyst (as disclosed further below), and any other modifying materials present in the reaction mass. Thus, hydrocarbons and chlorinated hydrocarbons are useful as vehicles in the invention. The hydrocarbons and chlorinated hydrocarbons are preferably saturated. Methylene chloride is a desirable vehicle in the practice of the invention.

The acylation with acetic anhydride can be carried out with an excess of acetic anhydride which performs the function of a vehicle in the reaction mass, although a substantial excess of the anhydride may cause a high degree of polyacylation. In order to minimize such polyacylation, an excess of the reactant, the trimethyl cyclododecatriene having the structure:

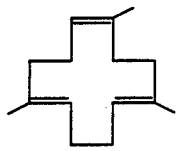

can be used in the reaction mixture.

The reaction is carried out in the presence of an acidic catalyst It has been found that Friedel-Crafts acylation agents are especially desirable as catalysts. Thus, boron trifluoride, boron trifluoride etherate, stannic chloride, ferric chloride and zinc chloride are preferred catalysts. The most preferred catalyst is boron trifluoride etherate. It will be understood that materials providing such catalysts under the reaction conditions can be used. In addition to the boron trifluoride ether complex, a boron trifluoride-acetic acid complex can also be used.

When a strong Friedel-Crafts acylation agent is used as a catalyst, a lower reaction temperature is desirable to facilitate control of the reaction velocity. When weaker Friedel-Crafts materials are used, a higher temperature is convenient and desirable to achieve a conveniently rapid reaction rate The reaction is accordingly carried out at temperatures ranging from below about −5° C. up to about 100° C. and in the range of from about −5° C. up to about 70° C. is preferred. Thus, with boron trifluoride, an ice bath at 0° C. can be used, and with stannic or ferric chloride temperatures on the order of 10° C.-50° C. are desirable. Zinc chloride gives good results at temperatures of about 70° C.

The concentration of the catalyst can vary from catalytic amounts, i.e., one or two percent of the reactant having the structure:

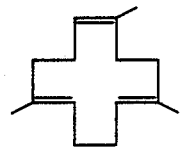

up to molar amounts. Stronger catalysts such as boron trifluoride can be used in lower concentrations, whereas it is generally advantageous to use higher concentrations of the weaker catalysts such as zinc chloride.

The times required will vary with the temperatures, concentrations of reactants and catalyst, and the particular reactants and catalyst used. The times utilized in the reaction vary from that sufficient to obtain a homogeneous mixture of the reaction mass to several hours, although this can be varied even more widely by controlling the reaction temperature, reaction materials, vehicles, and catalysts, as disclosed above. Thus, times preferably range from about 0.5 hours up to about 10 hours.

The reaction can be carried out at sub- or superatmospheric pressure This will vary according to the added vehicle, if any, contained in the reaction mixture, and the temperature, and it is generally preferred that the reaction be carried out at substantially atmospheric pressure.

After the reaction has been completed or carried out to the extent desired, the acetylated product is separated from the reaction mass. A preferred step in purification is removal of catalyst from the system by means of treatment with a suitable basic material. The basic material can either be a relatively strong one such as sodium hydroxide, or it can be a relatively weaker one, for example, the salt of a strong base and weaker acid, such as sodium carbonate, sodium acetate, and the like.

After catalyst removal, as described above, the reaction mass can be extracted to concentrate the desired products and/or it can be distilled. The partially purified material in a preferred aspect of the invention is then further purified by fractional distillation. If desired, other or further purification can be carried out by preparative chromatographic techniques.

Indeed, when desiring the pure compound having the structure:

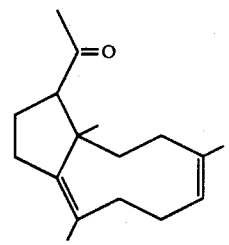

or a substantially pure version thereof, e.g., 98 or 99 percent compound having the structure:

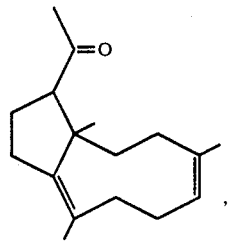

preparative chromatographic techniques are preferred.

The acylated bicycloalkadiene-compound-containing compositions of matter of our invention and one or more auxiliary perfume ingredients, including, for example, hydrocarbons, alcohols, ketones (other than the ketones of our invention), aldehydes, nitriles, esters, lactones, other hydrocarbons, synthetic essential oils and natural essential oils may be admixed so that the combined odors of the individual components produce a pleasant and desired fragrance particularly and preferably in the "patchouli, vetiver, woody, musky, amber" area. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling, fresh smelling materials.

In perfume compositions, it is the individual components which contribute to their particular olfactory characteristics, however the overall sensory effect of the perfume composition will be at least the sum total of the effects of each of the ingredients. Thus, the acylated bicycloalkadiene-compound-containing compositions of matter of our invention can be used to alter, modify or enhance the aroma characteristics of a perfume composition, for example, by utilizing or moderating the olfactory reaction contributed by another ingredient in the composition.

The amount of the acylated bicycloalkadiene-compound-containing compositions of matter of our invention which will be effective in perfume compositions as well as in perfumed articles and colognes depends upon many factors, including the other ingredients, their amounts and the effects which are desired. It has been found that perfume compositions containing as little as 0.005% of the acylated bicycloalkadiene-compound-containing compositions of matter of our invention or even less (e.g., 0.002%) can be used to impart a vetiver, peppery, woody, patchouli, musky, camphoraceous and amber aromas with sweet, musky, vetiver, peppery and ambery topnotes to soaps, cosmetics, detergents (including anionic, cationic, nonionic or zwitterionic solid or liquid detergents) or other products. The amount employed can range up to 70% of the fragrance components and will depend upon considerations of cost, nature of the end product, the effect desired on the finished product and the particular fragrance sought.

The acylated bicycloalkadiene-compound-containing compositions of matter of our invention are useful (taken alone or together with other ingredients in perfume compositions), in detergents and soaps, space odorants and deodorants, perfumes, colognes, toilet water, bath preparations such as lacquers, brilliantines, pomades and shampoos; cosmetic preparations such as creams, deodorants, hand lotions and sun screens; powders, such as talcs, dusting powders, face powders and the like.

As little as 0.7% of the acylated bicycloalkadiene-compound-containing compositions of matter of our invention will suffice to impart intense and substantive a vetiver, peppery, woody, patchouli, musky, camphoraceous and amber aromas, with sweet, musky, vetiver, peppery and ambery topnotes to sandalwood, patchouli and vetiver fragrance formulations. Generally, no more than 5% of the acylated bicycloalkadiene-compound-containing compositions of matter of our invention based on the ultimate end product are required to be used "as is" or in the perfume composition.

Furthermore, as little as 0.25% of one or more of the acylated bicycloalkadiene-compound-containing compositions of matter of our invention will suffice to impart such aroma to perfumed articles per se, whether in the presence of other perfume materials or whether used by themselves. Thus, the range of use of the acylated bicycloalkadiene-compound-containing compositions of matter of our invention in perfumed articles may vary from about 0.25% up to about 5% by weight based on the total weight of the perfumed article.

In addition, the perfume composition or fragrance composition of our invention can contain a vehicle, or carrier for the acylated bicycloalkadiene-compound-containing compositions of matter of our invention. The vehicle can be a liquid such as a non-toxic alcohol, e.g., ethanol, a non-toxic glycol, e.g., propylene glycol or the like. The carrier can also be an absorbent solid, such as a gum (e.g., gum arabic, guar gum or xanthan gum), or components for encapsulating the composition by means of coacervation (such as gelatin).

It will thus be apparent that the acylated bicycloalkadiene-compound-containing compositions of matter of our invention can be utilized to alter, modify or enhance the aroma of perfume compositions, colognes or perfumed articles.

The following Example A illustrates a process for producing a composition containing a substantial amount of the compound having the structure:

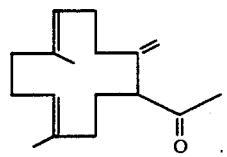

The following Example I serves to illustrate a process for producing the acylated bicycloalkadiene-compound-containing compositions of matter of our invention. Examples following Example I in general serve to illustrate organoleptic utilities of the acylated bicycloalkadiene-compound-containing compositions of matter of our invention.

In general, the following examples serve to illustrate specific embodiments of our invention. It will be understood that these examples are illustrative and that the invention is to be considered restricted thereto only as indicated in the appended claims.

All parts and percentages given herewith are by weight unless otherwise specified.

EXAMPLE A

Preparation of Acylated Cyclodecadiene Derivative

Reaction:

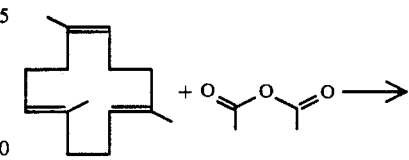

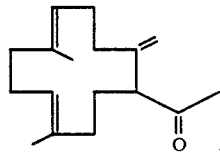

Into a 5 liter reaction flask equipped with stirrer, thermometer, reflux condenser, addition funnel and drying tube are charged the following materials:

1,250 ml Acetic anhydride;
1,550 ml BF3-etherate;
500 g 1,5,9-Trimethyl cyclododecatriene-1,5,9 as described below.

The flask is charged initially with acetic anhydride and BF3-etherate and then cooled to 0° C. At 0° C., the trimethyl cyclododecatriene is added. The reaction mass is stirred and made homogeneous, and is then poured onto 4,000 grams of ice. Thereafter, sodium hydroxide (5 percent aqueous) is added to neutralize the mass. The two resulting phases are separated, and the aqueous phase is extracted with benzene. The benzene extract is bulked with the main organic phase, and the benzene solvent is then stripped off. The weight of the resulting oil is 645 grams. The oil is then distilled. The ketonic product thus obtained has a boiling range of 180°-210° C. at 2 mm/Hg. and a persistent woody-amber fragrance.

On a scale of "1-10" the quality of the product is graded at 8; the intensity of the product is graded at 4; the substantivity of the product is graded at 3.

Figure 1:
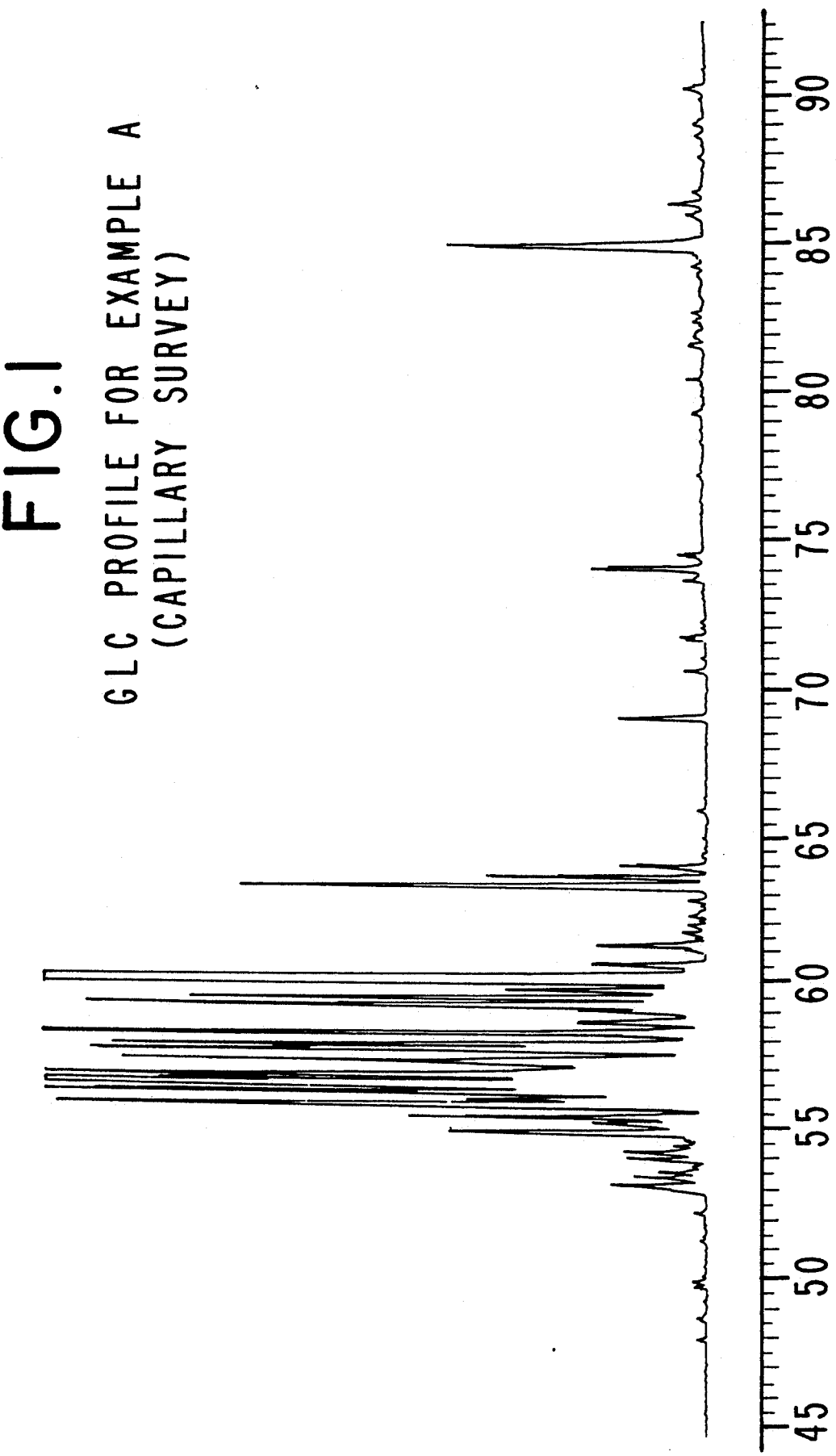
FIG. 1 is the GLC profile (capillary survey) for the reaction product of Example A containing a substantial quantity of the compound having the structure.

FIG. 1 is the GLC profile (capillary survey) of the reaction product.

EXAMPLE I

The Acylated Bicycloalkadiene-Compound-Containing Compositions of Matter of Our Invention Reaction:

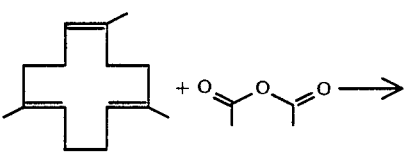

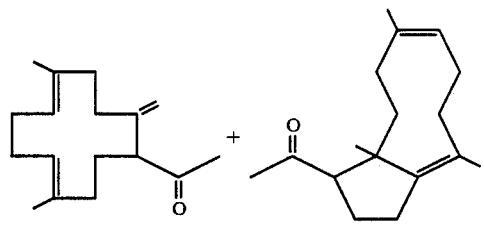

Into a 2 liter reaction vessel equipped with stirrer, thermometer, reflux condenser and heating mantle and cooling bath are placed 1,000 grams (6.0 moles) of the compound having the structure:

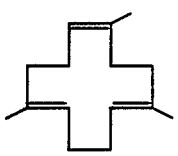

and 510 grams (5.0 moles) of acetic anhydride.

With stirring, the reaction mass is cooled to 0° C. Over a period of 0.5 hours, 20 grams of boron trifluoride etherate is added to the reaction mass while maintaining the reaction mass at 0° C.

The reaction mass is stirred at 5°-10° C. for a period of two hours.

At the end of the two hour period, the reaction mass is quenched with water and made basic with 20 grams of a 5 molar sodium hydroxide solution. The organic phase is separated from the aqueous phase and the organic phase is washed with 1,000 cc of water. The organic phase is separated from the aqueous phase and the organic phase is distilled on a 4" splash column yielding the following fractions:

| Fraction No. | Vapor Temp. (°C.) | Liquid Temp. (°C.) | Vacuum mm/Hg. Pressure |
|---|---|---|---|
| 1 | 110/120 | 130/140 | 2.5/2.5 |
| 2 | 130 | 150 | 2.5 |
| 3 | 145 | 175 | 2.5 |
| 4 | 148 | 180 | 2.0. |

Fractions 2, 3 and 4 are bulked and redistilled on a 12" Goodloe column yielding the following fractions:

| Fraction No. | Vapor Temp. (°C.) | Liquid Temp. (°C.) | Vacuum mm/Hg. Pressure |
|---|---|---|---|
| 1 | 98/108 | 115/120 | 3.5/3.0 |
| 2 | 108 | 120 | 3.0 |
| 3 | 108 | 125 | 3.0 |
| 4 | 110 | 130 | 3.0 |
| 5 | 115 | 140 | 3.0 |
| 6 | 115 | 145 | 3.0 |
| 7 | 135 | 145 | 3.0 |
| 8 | 135 | 151 | 3.0 |
| 9 | 139 | 151 | 3.0 |
| 10 | 139 | 156 | 3.0 |
| 11 | 140 | 165 | 3.0 |
| 12 | 140 | 168 | 3.0 |
| 13 | 140 | 180 | 3.0. |

Fractions 9-13 are bulked.

Bulked distillation Fractions 9-13 have a vetiver, peppery, woody, patchouli, musky, camphoraceous and amber aroma, with sweet, musky, vetiver, peppery and ambery topnotes.

The quality of the product on a scale of 1-10 is as follows:
quality: 9;
intensity: 9; and
substantivity: 9.

FIG. 2 is the GLC profile (capillary survey) for the reaction product.

FIG. 3 is the GLC profile for the reaction product also (bulked distillation Fractions 9-13). The peak indicated by reference 31 is the peak for the compound having the structure:

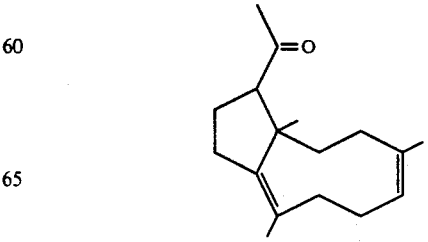

(greater than 50% of the reaction product). The peak indicated by reference 33 is the peak for the compound having the structure:

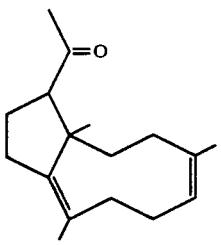

(less than 50% of the reaction product).

FIG. 4 is the NMR spectrum for the peak indicated by reference numeral 31 of FIG. 3 for the compound having the structure:

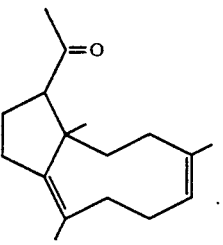

FIG. 5 is the infr-red spectrum for peak 31 of FIG. 3 for the compound having the structure:

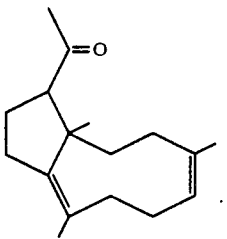

FIG. 6 is the NMR spectrum for the compound having the structure:

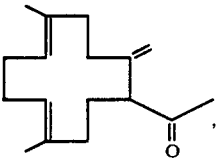

peak 33 of FIG. 3.

FIG. 7 is the infr-red spectrum for the compound having the structure:

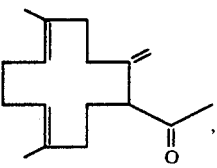

peak 33 of FIG. 3.

EXAMPLE II

Woody Amber Fragrance

The following composition is prepared:

| Ingredients | Parts by Weight |
|---|---|
| Cassia absolute | 60 |
| Methyl ionone | 60 |
| Jasmine extra | 80 |
| Neroli oil, bigarade | 60 |
| Patchouli oil | 60 |
| Vanillin | 60 |
| Product of Example I, bulked distillation Fractions 9-13 containing the compounds having the structures: | 30 |

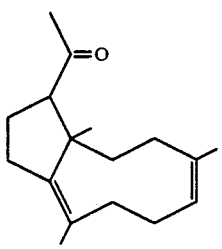

(greater than 50%) and

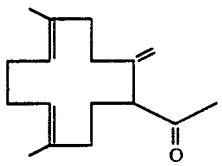

(less than 50%).

| | |
|---|---|
| Lemon oil | 80 |
| Rose geranium oil | 120 |
| Lavender oil, French | 120 |
| Sweet orange oil | 80 |
| Musk extract, (3% in Diethylphthalate) | 50 |
| Civet extract, (3% in Diethylphthalate) | 50 |

The mixture of compounds prepared according to Example I bulked distillation Fractions 9-13 imparts to this woody, amber aroma excellent vetiver, peppery, patchouli, musky and camphoraceous undertones and sweet, musky, vetiver and peppery topnotes. Accordingly, the fragrance can be described as "woody, amber with vetiver, peppery, patchouli, musky and camphoraceous undertones and sweet, musky, vetiver and peppery topnotes".

EXAMPLE III

Preparation of Cosmetic Powder Compositions

Cosmetic powder compositions are prepared by mixing in a ball mill 100 grams of talcum powder with 0.25 grams of each of the substances set forth in Table I below. Each of the cosmetic powder compositions has an excellent aroma as described in Table I below:

TABLE I

| Substance | Aroma Description |
|---|---|
| Mixture of compounds prepared according | A vetiver, peppery, woody, patchouli, musky and |

TABLE I-continued

| Substance | Aroma Description |
|---|---|
| to Example I, bulked distillation Fractions 9-13 containing compounds having the structures: | camphoraceous aroma with sweet, musky, vetiver, peppery and ambery topnotes. |

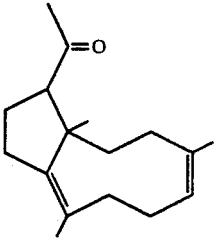

(greater than 50%) and

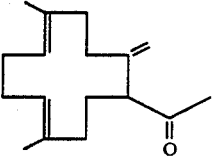

| | |
|---|---|
| (less than 50%). Perfume composition of Example II. | Woody, amber with vetiver, peppery, patchouli, musky and camphoraceous undertones and sweet, musky, vetiver and peppery topnotes. |

EXAMPLE IV

Perfumed Liquid Detergents

Concentrated liquid detergents (Lysine salt of n-dodecyl-benzene sulfonic acid as more specifically described in U.S. Letter Pat. No. 3,948,818 issued on April 6, 1976) with aroma nuances as set forth in Table I of Example III are prepared containing 0.10%, 0.15%, 0.20%, 0.25%, 0.30% and 0.35% of the substance set forth in Table I of Example III. They are prepared by adding and homogeneously mixing the appropriate quantity of substance set forth in Table I of Example III in the liquid detergent. The detergents all possess excellent aromas as set forth in Table I of Example III, the intensity increasing with greater concentration of substance as set forth in Table I of Example III.

EXAMPLE V

Preparation of Colognes and Handkerchief Perfume

Compositions as set forth in Table I of Example III are incorporated into colognes at concentrations of 2.0%, 2.5%, 3.0%, 3.5%, 4.0%, 4.5% and 5.0% in 80%, 85%, 90% and 95% aqueous food grade ethanol solutions; and into handkerchief perfumes at concentrations of 15%, 20%, 25% and 30% (in 80%, 85%, 90% and 95% aqueous food grade ethanol solutions). Distinctive and definitive fragrances as set forth in Table I of Example III are imparted to the colognes and to the handkerchief perfumes at all levels indicated.

EXAMPLE VI

Preparation of Soap Compositions

One hundred grams of soap chips [per sample]- (IVORY ®, produced by the Procter & Gamble Company of Cincinnati, Ohio), are each mixed with one gram samples of substances as set forth in Table I of Example III until homogeneous compositions are obtained. In each of the cases, the homogeneous compositions are heated under 8 atmospheres pressure at 180° C. for a period of three hours and the resulting liquids are placed into soap molds. The resulting soap cakes, on cooling, manifest aromas as set forth in Table I of Example III.

EXAMPLE VII

Preparation Of Solid Detergent Compositions

Detergents are prepared using the following ingredients according to Example I of Canadian Patent No. 1,007,948:

| Ingredient | Percent by Weight |
|---|---|
| "NEODOL ®" 45-11 (a $C_{14}$-$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

This detergent is a phosphate-free detergent. Samples of 100 grams each of this detergent are admixed with 0.10, 0.15, 0.20 and 0.25 grams of each of the substances as set forth in Table I of Example III. Each of the detergent samples has an excellent aroma as indicated in Table I of Example III.

EXAMPLE VIII

Utilizing the procedure of Example I at column 15 of U.S. Letter Pat. No. 3,632,396, non-woven cloth substrates useful as drier-added fabric softening articles of manufacture are prepared wherein the substrate, the substrate coating and the outer coating and the perfuming material are as follows:

1. A water "dissolvable" paper ("Dissolvo Paper");
2. Adogen 448 (m.p. about 140° F.) as the substrate coating; and
3. An outer coating having the following formulation (m.p. about 150° F.):
   57% $C_{20\text{-}22}$ HAPS;
   22% isopropyl alcohol;
   20% antistatic agent
   1% of one of the substances as set forth in Table I of Example III.

Fabric softening compositions prepared according to Example I at column 15 of U.S. Letter Pat. No. 3,632,396 having aroma characteristics as set forth in Table I of Example III, consist of a substrate coating having a weight of about 3 grams per 100 square inches of substrate; a first coating on the substrate coating consisting of about 1.85 grams per 100 square inches of substrate; and an outer coating coated on the first coating consisting of about 1.4 grams per 100 square inches of substrate. One of the substances of Table I of Example III is admixed in each case with the outer coating mixture, thereby providing a total aromatized outer coating weight ratio to substrate of about 0.5:1 by weight of the substrate The aroma characteristics are imparted in a pleasant manner to the head space in a dryer on operation thereof in each case using said drier-added fabric softener non-woven fabrics and these aroma characteristics are described in Table I of Example III.

EXAMPLE IX

Hair Spray Formulations

The following hair spray formulation is prepared by first dissolving PVP/VA E-735 copolymer manufactured by the GAF Corporation of 140 West 51st Street, New York, New York, in 91.62 grams of 95% food grade ethanol, 8.0 grams of the polymer is dissolved in the alcohol. The following ingredients are added to the PVP/VA alcoholic solution:

| Ingredient | Weight Percent |
| --- | --- |
| Dioctyl sebacate | 0.05 |
| Benzyl alcohol | 0.10 |
| Dow Corning 473 fluid (prepared by Dow Corning Corporation) | 0.10 |
| TWEEN ® 20 surfactant (prepared by I.C.I. America Corporation) | 0.03 |
| One of the perfumery substance as set forth in Table I of Example III. | 0.10 |

The perfuming substances as set forth in Table I of Example III add aroma characteristics as set forth in Table I of Example III which are rather intense and aesthetically pleasing to the users of the soft-feel, good-hold pump hair sprays.

EXAMPLE X

Conditioning Shampoos

Monamid CMA (prepared by the Mona Industries Company)(3.0 weight percent) is melted with 2.0 weight percent coconut fatty acid (prepared by Procter & Gamble Company of Cincinnati, Ohio); 1.0 weight percent ethylene glycol distearate (prepared by the Armak Corporation) and triethanolamine (a product of Union Carbide Corporation)(1.4 weight percent). The resulting melt is admixed with Stepanol WAT produced by the Stepan Chemical Company (35.0 weight percent). The resulting mixture is heated to 60° C. and mixed until a clear solution is obtained (at 60° C.).

GAFQUAT ®755N polymer (manufactured by GAF Corporation of 140 West 51st Street, New York, New York)(5.0 weight percent) is admixed with 0.1 weight percent sodium sulfite and 1.4 weight percent polyethylene glycol 6000 distearate produced by Armak Corporation.

The resulting material is then mixed and cooled to 45° C. and 0.3 weight percent of perfuming substance as set forth in Table I of Example III is added to the mixture. The resulting mixture is cooled to 40° C. and blending is carried out for an additional one hour in each case. At the end of this blending period, the resulting material has a pleasant fragrance as indicated in Table I of Example III.

What is claimed is:

1. The compound having the structure:

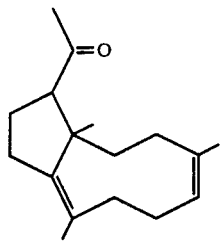

2. A mixture of compounds having the structures:

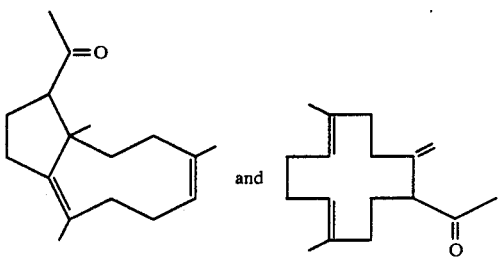

wherein the compound having the structure:

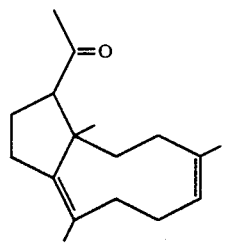

is in an amount greater than 50% of the mixture.

3. The product produced according to the process of reacting the compound having the structure:

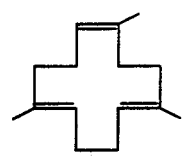

with acetic anhydride in the presence of a Lewis acid catalyst to produce a mixture of compounds containing compounds having the structures:

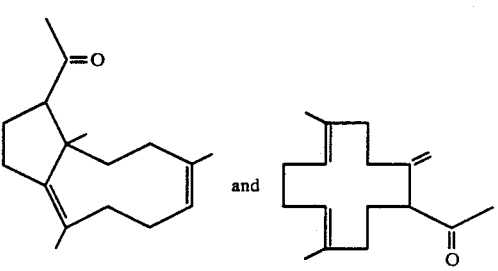

wherein the compound having the structure:

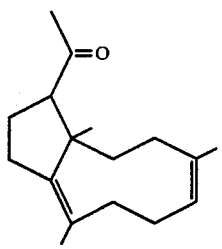

is in amount greater than 50%.

4. The product produced according to the process of claim 3 wherein the Lewis acid catalyst used in the process for producing said product is boron trifluoride etherate.

5. A perfume composition comprising a perfume base and intimately admixed therewith a perfuming quantity of a composition of matter of claim 1.

6. A perfume composition comprising a perfume base and intimately admixed therewith a perfuming quantity of a composition of matter of claim 2.

7. A perfume composition comprising a perfume base and intimately admixed therewith a perfuming quantity of a composition of matter of claim 3.

8. A perfume composition comprising a perfume base and intimately admixed therewith a perfuming quantity of a composition of matter of claim 4.

9. A process for augmenting or enhancing the aroma of a fragrance composition, cologne or perfumed article comprising the step of intimately admixing with said fragrance composition, cologne or perfumed article, an aroma augmenting or enhancing quantity of the composition of matter of claim 1.

10. A process for augmenting or enhancing the aroma of a fragrance composition, cologne or perfumed article comprising the step of intimately admixing with said fragrance composition, cologne or perfumed article, an aroma augmenting or enhancing quantity of the composition of matter of claim 2.

11. A process for augmenting or enhancing the aroma of a fragrance composition, cologne or perfumed article comprising the step of intimately admixing with said fragrance composition, cologne or perfumed article, an aroma augmenting or enhancing quantity of the composition of matter of claim 3.

12. A process for augmenting or enhancing the aroma of a fragrance composition, cologne or perfumed article comprising the step of intimately admixing with said fragrance composition, cologne or perfumed article, an aroma augmenting or enhancing quantity of the composition of matter of claim 4.

* * * * *